(12) United States Patent
Vignon et al.

(10) Patent No.: US 11,719,797 B2
(45) Date of Patent: Aug. 8, 2023

(54) METHODS AND SYSTEMS FOR CONTROLLING THE GENERATION OF A COMPOUND ULTRASOUND IMAGE

(71) Applicant: KONINKLIJKE PHILIPS N.V., Eindhoven (NL)

(72) Inventors: Francois Guy Gerard Marie Vignon, Andover, MA (US); Sheng-Wen Huang, Ossining, NY (US); Jun Seob Shin, Medford, MA (US); Darwin Philip Adams, Lexington, MA (US); Scott William Dianis, Andover, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 786 days.

(21) Appl. No.: 16/612,387

(22) PCT Filed: May 11, 2018

(86) PCT No.: PCT/EP2018/062259
§ 371 (c)(1),
(2) Date: Nov. 10, 2019

(87) PCT Pub. No.: WO2018/206797
PCT Pub. Date: Nov. 15, 2018

(65) Prior Publication Data
US 2020/0200886 A1    Jun. 25, 2020

Related U.S. Application Data

(60) Provisional application No. 62/504,692, filed on May 11, 2017.

(51) Int. Cl.
*G01S 7/52* (2006.01)
*G06T 7/514* (2017.01)
(Continued)

(52) U.S. Cl.
CPC ...... *G01S 7/52085* (2013.01); *G01S 7/52025* (2013.01); *G06T 5/002* (2013.01);
(Continued)

(58) Field of Classification Search
USPC ................ 367/7; 382/260, 128; 600/458
See application file for complete search history.

(56) References Cited

U.S. PATENT DOCUMENTS

| 5,997,479 | A | 12/1999 | Savord et al. |
| 6,013,032 | A | 1/2000 | Savord |

(Continued)

FOREIGN PATENT DOCUMENTS

| EP | 2702946 A1 | 3/2014 |
| JP | 2015077216 A | 4/2015 |
| WO | 2013128301 A2 | 9/2013 |

OTHER PUBLICATIONS

PCT/EP/2018/062259 ISR & WO, Jul. 26, 2018, 16 Page Document.

*Primary Examiner* — Kathleen Y Dulaney

(57) ABSTRACT

The invention provides a method for controlling the generation of a compound ultrasonic image. The method includes obtaining a first ultrasound image and applying adaptive beamforming to the first ultrasound image, thereby generating a second ultrasound image. A weighting is determined based on the first and second ultrasound images, wherein the weighting comprises at least one weighting component. The compound ultrasound image is then generated based on the first and second ultrasound images and the weighting component.

4 Claims, 3 Drawing Sheets

(51) Int. Cl.
  *G06T 5/00* (2006.01)
  *G06T 5/20* (2006.01)
  *G06T 5/50* (2006.01)
  *A61B 8/06* (2006.01)
  *A61B 8/14* (2006.01)
  *A61B 8/00* (2006.01)
  *A61B 8/08* (2006.01)

(52) U.S. Cl.
  CPC .................. *G06T 5/20* (2013.01); *G06T 5/50* (2013.01); *G06T 7/514* (2017.01); *A61B 8/06* (2013.01); *A61B 8/145* (2013.01); *A61B 8/463* (2013.01); *A61B 8/483* (2013.01); *A61B 8/488* (2013.01); *G06T 2200/24* (2013.01); *G06T 2207/10132* (2013.01); *G06T 2207/20224* (2013.01)

(56) References Cited

U.S. PATENT DOCUMENTS

| | | | |
|---|---|---|---|
| 6,283,919 B1 | 9/2001 | Roundhill et al. | |
| 6,443,896 B1 | 9/2002 | Detmer | |
| 6,458,083 B1 | 10/2002 | Jago et al. | |
| 6,530,885 B1 | 3/2003 | Entrekin et al. | |
| 7,744,532 B2 * | 6/2010 | Ustuner | G01S 15/8927 600/443 |
| 8,045,777 B2 | 10/2011 | Zwirn | |
| 9,299,172 B2 * | 3/2016 | Koehler | G06T 5/002 |
| 2002/0045822 A1 | 4/2002 | Powers et al. | |
| 2013/0258805 A1 * | 10/2013 | Hansen | G01S 7/52046 367/8 |
| 2014/0063002 A1 * | 3/2014 | Nagae | A61B 8/461 345/419 |
| 2014/0064021 A1 * | 3/2014 | Nagae | A61B 8/463 367/7 |
| 2014/0240482 A1 * | 8/2014 | Ikeda | H04N 23/632 348/77 |
| 2015/0025385 A1 * | 1/2015 | Ikeda | G01S 15/8915 600/443 |
| 2015/0119682 A1 * | 4/2015 | Nagae | A61B 5/0091 600/407 |
| 2016/0124082 A1 * | 5/2016 | Masuda | G01S 15/8915 367/87 |
| 2017/0042509 A1 * | 2/2017 | Ikeda | G01N 29/262 |
| 2018/0021013 A1 * | 1/2018 | Suzuki | A61B 8/4488 600/459 |
| 2019/0129026 A1 * | 5/2019 | Sumi | G01S 15/8915 |

* cited by examiner

METHODS AND SYSTEMS FOR CONTROLLING THE GENERATION OF A COMPOUND ULTRASOUND IMAGE

CROSS-REFERENCE TO PRIOR APPLICATIONS

This application is the U.S. National Phase application under 35 U.S.C. § 371 of International Application No. PCT/EP2018/062259, filed on May 11, 2018, which claims the benefit of U.S. Provisional Patent Application No. 62/504,692, filed on May 11, 2017. These applications are hereby incorporated by reference herein.

RELATED APPLICATION

This application claims the benefit of and priority to U.S. Provisional No. 62/504,692, filed May 11, 2017, which is incorporated by reference in its entirety.

FIELD OF THE INVENTION

This invention relates to the field of ultrasonic imaging, and more specifically to the field of generating compound ultrasonic images.

BACKGROUND OF THE INVENTION

Ultrasound imaging is increasingly being employed in a variety of different applications. It is important that the image produced by the ultrasound system is as clear and accurate as possible so as to give the user a realistic interpretation of the subject being scanned. This is especially the case when the subject in question is a patient undergoing a medical ultrasound scan. In this situation, the ability of a doctor to make an accurate diagnosis is dependent on the quality of the image produced by the ultrasound system.

Adaptive beamforming techniques, such as minimum variance (MV) beamforming, have been developed and applied to ultrasound imaging to achieve an improvement in image quality; however, MV beamforming is computationally intensive as an inversion of the spatial covariance matrix is required for each pixel of the image. In addition, even though MV beamforming is developed primarily for an improvement in spatial resolution, and is not ideal for reducing off-axis clutter, its performance in terms of improving spatial resolution often needs to be sacrificed by reducing the subarray size. Otherwise, image artifacts may occur in the speckle due to signal cancellation.

Adaptive weighting techniques, such as: the coherence factor (CF); the generalized coherence factor (GCF); the phase coherence factor (PCF); and the short-lag spatial coherence (SLSC), have been proposed but all require access to per-channel data to compute a weighting mask to be applied to the image. Further, these methods would only work for conventional imaging with focused transmit beams and are not suitable for plane wave imaging (PWI) or diverging wave imaging (DWI) involving only a few transmits.

SUMMARY OF THE INVENTION

Many adaptive beamforming techniques, including coherence—based weighting, Minimum Variance beamforming eliminate image clutter at the expense of an increased speckle variance. Dark areas of speckle are usually incoherent across the aperture, causing them to be rejected further by the adaptive beamforming techniques. Whilst the clutter rejection capability is beneficial, the increase in speckle variance can be a significant drawback. The acceptable level of speckle variance varies per clinician, based on personal image perception, and also per clinical application.

There is therefore a need for a method for controlling the generation of a compound ultrasound image, which may provide a more optimal balance between clutter rejection and speckle noise variance.

The invention is defined by the claims.

According to examples in accordance with an aspect of the invention, there is provided a method for controlling the generation of a compound ultrasonic image, the method comprising:

obtaining a first ultrasound image;

applying adaptive beamforming to the first ultrasound image, thereby generating a second ultrasound image;

determining a weighting based on the first and second ultrasound images, wherein the weighting comprises at least one weighting component; and generating the compound ultrasound image based on the first and second ultrasound images and the at least one weighting component.

This method performs a weighted combination of a first ultrasound image, which has not undergone adaptive beamforming, and a second ultrasound image, which has undergone adaptive beamforming.

By adjusting the weighting in favor of the second ultrasound image, the clutter in the compound ultrasound will be reduced; however, the speckle variance will be increased. By adjusting the weighting in favor of the first ultrasound image, the variance in the speckle of the compound image is reduced; however, the clutter will be increased. In this way, it is possible to determine an optimal weighting between the two images to be combined. In other words, the weighting may act as a ratio for combining the first and second ultrasound images. The weighting may be determined automatically based on previous results, or may be manually adjusted.

In an embodiment, the generating of the compound ultrasound image comprises:

applying a first weighting component to the first ultrasound image;

applying a second weighting component to the second ultrasound image; and summing the weighted first and second ultrasound images, thereby generating the compound ultrasound image.

By applying a first and second weighting component to the first and second images, it is possible to fine-tune the contribution of each ultrasound image to the compound ultrasound image. These weighted contributions may then be summed to form the final compound image.

In a further embodiment, the first and second weighting components depend on a first tuning parameter.

In this way, it is possible to control the weighting components by way of a single tuning parameter. For example, a user would only be required to alter a single factor in order to change the weighting components, thereby making the control of the weighting components easier.

In an embodiment, the method further comprises:

applying a low pass filter or speckle smoothing filter to the first and second ultrasound images, thereby generating a first image approximation and a second image approximation;

generating a first detail image, based on the first image approximation and the first ultrasound image; and generating a second detail image, based on the second image approximation and the second ultrasound image.

In this way, the generation of the compound ultrasound image may be controlled at different spatial scales, or its effect on speckle and structures may be separated. For example, by applying a low pass filter to the first and second ultrasound images, the low spatial frequencies of the images may be isolated from the high spatial frequencies, thereby forming first and second image approximations. The low spatial frequencies typically contain the image clutter. In a further example, a speckle smoothing filter, such as a Lee filter, may be used to reduce the speckle in the first and second ultrasound images.

In a further embodiment, the generating of the first and second detail images comprises:

subtracting the first image approximation from the first ultrasound image, thereby generating the first detail image; and subtracting the second image approximation from the second ultrasound image, thereby generating the second detail image.

By subtracting the image approximations, containing the low spatial frequencies, from the ultrasound images, it is possible to isolate the high spatial frequencies of the ultrasound images. The high spatial frequencies typically contain the speckle noise and high-resolution objects of the image. If a resolution-preserving speckle filter is used instead, it is possible to isolate the structures from the speckle in the ultrasound images.

In an arrangement, the generating of the compound ultrasound image comprises:

applying a third weighting component to the first image approximation;

applying a fourth weighting component to the second image approximation;

applying a fifth weighting component to the first detail image;

applying a sixth weighting component to the second detail image; and summing the weighted first and second detail images and first and second image approximations, thereby generating the compound ultrasound image.

By separating the low and high spatial frequencies of the ultrasound images and applying separate weighting components to each image contribution; it is possible to further control the generation of the compound ultrasound image.

In a further arrangement, the third and fourth weighting components depend on a second tuning parameter, and, wherein the fifth and sixth weighting component depend of a third tuning parameter In this way, it is possible to control the weighting components applied to the low spatial frequency components or structure components of the ultrasound images, by way of a single tuning parameter, and the weighting components applied to the high spatial frequency components or speckle components of the ultrasound images by way of a separate single tuning parameter. By providing two independent tuning parameters, it is possible to simply control the contributions of the image approximations and detail images to the compound ultrasound image. For example, a user would only be required to alter two factors in order to change the four weighting components, thereby making the control of the weighting components easier.

In an embodiment, the weighting components and the generating of the compound ultrasound image are depth-dependent.

In this way, it is possible to separately control the weighting components applied to the first and second ultrasound images at different depths. For example, the first ultrasound image may be preferentially weighted at deeper depths and the second ultrasound image may be preferentially weighted at shallower depths.

According to examples in accordance with an aspect of the invention, there is provided a computer program comprising computer program code means which is adapted, when said computer is run on a computer, to implement the method described above.

According to examples in accordance with an aspect of the invention, there is provided a controller for controlling the generation of a compound ultrasonic image, wherein the controller is adapted to:

obtain a first ultrasound image;

apply adaptive beamforming to the first ultrasound image, thereby generating a second ultrasound image;

determine a weighting based on the first and second ultrasound images, wherein the weighting comprises at least one weighting component; and generate the compound ultrasound image based on the first and second ultrasound images and the at least one weighting component.

According to examples in accordance with an aspect of the invention, there is provided an ultrasound system comprising:

an ultrasonic transducer array, wherein the ultrasonic transducer array is capable of emitting and receiving ultrasonic signals;

a signal processor for compiling the received ultrasonic signals into an ultrasound image;

a controller as described above;

a user interface in communication with the controller; and an image output device for outputting the filtered ultrasound image.

In an embodiment, the controller is adapted to alter the weighting based on a user input at the user interface.

In this way, a user may directly alter the weighting by way of the user interface. The user interface may comprise a digital display, which may indicate the current image weightings and allow the user to alter said weightings.

In an arrangement, the controller is further adapted to control different weighting components at different depths based on a user input at the user interface.

In this way, the user is provided with greater control over the compositions of the final ultrasound image.

In some designs, the user interface comprises a dial or slider.

The dial and/or slider may be a physical component of the system, or may be incorporated as part of a digital display. By providing a dial and/or slider, the user may easily adjust the weightings of the compound ultrasound image contributions. The dial and/or slider may incrementally alter the weightings. Alternatively, they may comprise a continuous scale, thereby allowing the user finer control of the weightings.

In an embodiment, the controller is adapted to obtain a predetermined weighting from a plurality of predetermined weightings.

In this way, the system may be quickly and easily initialized by selecting a previously tested weighting to form the compound ultrasound image. The system may be adapted to store a previously used set of weightings. In this case, the user interface may comprise a selection means adapted to select the predetermined weighting.

The selection means may, for example, comprise a button, or in the case of the user interface including a digital display, a checkbox. Alternatively, the dial and/or slider may include an additional operation mode, for example by way of a button, which enables the user to select predetermined settings.

BRIEF DESCRIPTION OF THE DRAWINGS

Examples of the invention will now be described in detail with reference to the accompanying drawings, in which.

DETAILED DESCRIPTION OF THE EMBODIMENTS

The invention provides a method for controlling the generation of a compound ultrasonic image. The method includes obtaining a first ultrasound image and applying adaptive beamforming to the first ultrasound image, thereby generating a second ultrasound image. A weighting is determined based on the first and second ultrasound images, wherein the weighting comprises a weighting component. The compound ultrasound image is then generated based on the first and second ultrasound images and the weighting.

Figure 1:
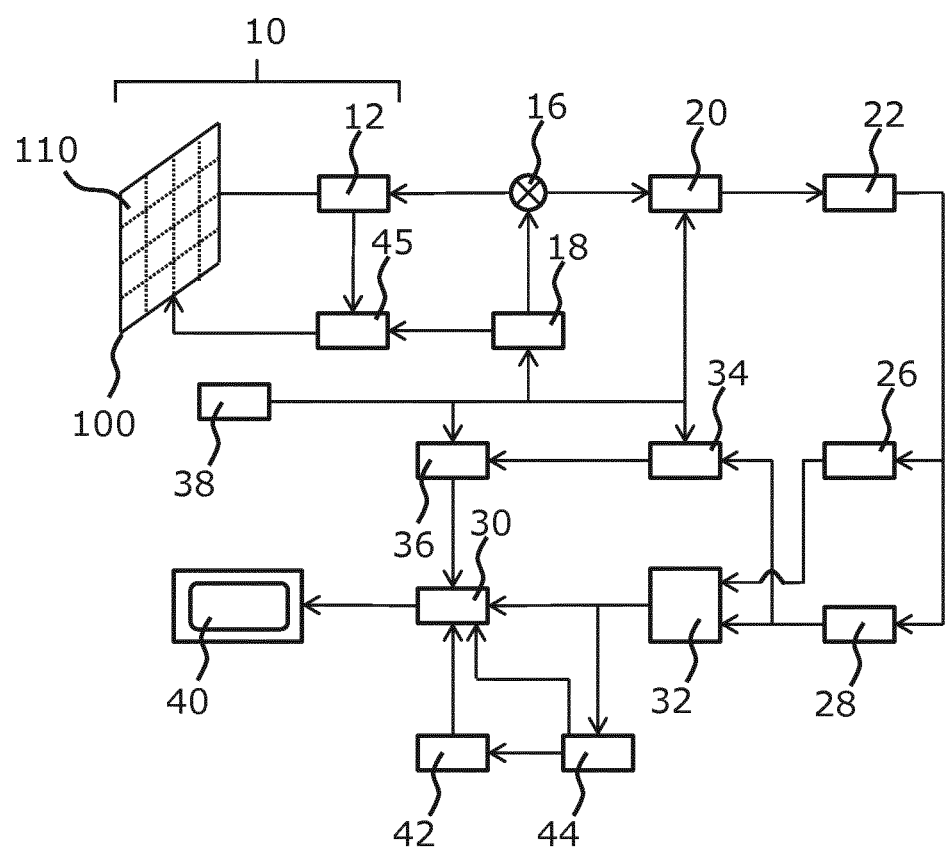
FIG. 1 shows an ultrasound diagnostic imaging system to explain the general operation.

The general operation of an exemplary ultrasound diagnostic imaging system will first be described, with reference to FIG. 1, and with emphasis on the signal processing function of the system since this invention relates to the processing of the signals measured by the transducer array.

The system comprises an array transducer probe 10 which has a CMUT transducer array 100 for transmitting ultrasound waves and receiving echo information. The transducer array 100 may alternatively comprise piezoelectric transducers formed of materials such as PZT or PVDF. The transducer array 100 is a two-dimensional array of transducers 110 capable of scanning in a 2D plane or in three dimensions for 3D imaging. In another example, the transducer array may be a 1D array.

The transducer array 100 is coupled to a microbeamformer 12 in the probe which controls reception of signals by the CMUT array cells or piezoelectric elements. Microbeamformers are capable of at least partial beamforming of the signals received by subarrays (or "groups" or "patches") of transducers as described in U.S. Pat. No. 5,997,479 (Savord et al.), U.S. Pat. No. 6,013,032 (Savord), and U.S. Pat. No. 6,623,432 (Powers et al.).

Note that the microbeamformer is entirely optional. The examples below assume no analog beamforming.

The microbeamformer 12 is coupled by the probe cable to a transmit/receive (T/R) switch 16 which switches between transmission and reception and protects the main beamformer 20 from high energy transmit signals when a microbeamformer is not used and the transducer array is operated directly by the main system beamformer. The transmission of ultrasound beams from the transducer array 10 is directed by a transducer controller 18 coupled to the microbeamformer by the T/R switch 16 and a main transmission beamformer (not shown), which receives input from the user's operation of the user interface or control panel 38.

One of the functions controlled by the transducer controller 18 is the direction in which beams are steered and focused. Beams may be steered straight ahead from (orthogonal to) the transducer array, or at different angles for a wider field of view. The transducer controller 18 can be coupled to control a DC bias control 45 for the CMUT array. The DC bias control 45 sets DC bias voltage(s) that are applied to the CMUT cells.

In the reception channel, partially beamformed signals are produced by the microbeamformer 12 and are coupled to a main receive beamformer 20 where the partially beamformed signals from individual patches of transducers are combined into a fully beamformed signal. For example, the main beamformer 20 may have 128 channels, each of which receives a partially beamformed signal from a patch of dozens or hundreds of CMUT transducer cells or piezoelectric elements. In this way the signals received by thousands of transducers of a transducer array can contribute efficiently to a single beamformed signal.

The beamformed reception signals are coupled to a signal processor 22. The signal processor 22 can process the received echo signals in various ways, such as band-pass filtering, decimation, I and Q component separation, and harmonic signal separation which acts to separate linear and nonlinear signals so as to enable the identification of nonlinear (higher harmonics of the fundamental frequency) echo signals returned from tissue and micro-bubbles. The signal processor may also perform additional signal enhancement such as speckle reduction, signal compounding, and noise elimination. The band-pass filter in the signal processor can be a tracking filter, with its pass band sliding from a higher frequency band to a lower frequency band as echo signals are received from increasing depths, thereby rejecting the noise at higher frequencies from greater depths where these frequencies are devoid of anatomical information.

The beamformers for transmission and for reception are implemented in different hardware and can have different functions. Of course, the receiver beamformer is designed to take into account the characteristics of the transmission beamformer. In FIG. 1 only the receiver beamformers 12, 20 are shown, for simplicity. In the complete system, there will also be a transmission chain with a transmission micro beamformer, and a main transmission beamformer.

The function of the micro beamformer 12 is to provide an initial combination of signals in order to decrease the number of analog signal paths. This is typically performed in the analog domain.

The final beamforming is done in the main beamformer 20 and is typically after digitization.

The transmission and reception channels use the same transducer array 10' which has a fixed frequency band. However, the bandwidth that the transmission pulses occupy can vary depending on the transmission beamforming that has been used. The reception channel can capture the whole transducer bandwidth (which is the classic approach) or by using bandpass processing it can extract only the bandwidth that contains the useful information (e.g. the harmonics of the main harmonic).

The processed signals are coupled to a B mode (i.e. brightness mode, or 2D imaging mode) processor 26 and a Doppler processor 28. The B mode processor 26 employs detection of an amplitude of the received ultrasound signal for the imaging of structures in the body such as the tissue of organs and vessels in the body. B mode images of structure of the body may be formed in either the harmonic image mode or the fundamental image mode or a combination of both as described in U.S. Pat. No. 6,283,919 (Roundhill et al.) and U.S. Pat. No. 6,458,083 (Jago et al.) The Doppler processor 28 processes temporally distinct signals from tissue movement and blood flow for the detection of the motion of substances such as the flow of blood cells in the image field. The Doppler processor 28 typically includes a wall filter with parameters which may be set to pass and/or reject echoes returned from selected types of materials in the body.

The structural and motion signals produced by the B mode and Doppler processors are coupled to a scan converter 32 and a multi-planar reformatter 44. The scan converter 32 arranges the echo signals in the spatial relationship from which they were received in a desired image format. For instance, the scan converter may arrange the echo signal into a two dimensional (2D) sector-shaped format, or a pyramidal three dimensional (3D) image. The scan converter can overlay a B mode structural image with colors corresponding to motion at points in the image field with their Doppler-estimated velocities to produce a color Doppler image which depicts the motion of tissue and blood flow in the image field. The multi-planar reformatter will convert echoes which are received from points in a common plane in a volumetric region of the body into an ultrasound image of that plane, as described in U.S. Pat. No. 6,443,896 (Detmer). A volume renderer 42 converts the echo signals of a 3D data set into a projected 3D image as viewed from a given reference point as described in U.S. Pat. No. 6,530,885 (Entrekin et al.).

The 2D or 3D images are coupled from the scan converter 32, multi-planar reformatter 44, and volume renderer 42 to an image processor 30 for further enhancement, buffering and temporary storage for display on an image display 40. In addition to being used for imaging, the blood flow values produced by the Doppler processor 28 and tissue structure information produced by the B mode processor 26 are coupled to a quantification processor 34. The quantification processor produces measures of different flow conditions such as the volume rate of blood flow as well as structural measurements such as the sizes of organs and gestational age. The quantification processor may receive input from the user control panel 38, such as the point in the anatomy of an image where a measurement is to be made. Output data from the quantification processor is coupled to a graphics processor 36 for the reproduction of measurement graphics and values with the image on the display 40, and for audio output from the display device 40. The graphics processor 36 can also generate graphic overlays for display with the ultrasound images. These graphic overlays can contain standard identifying information such as patient name, date and time of the image, imaging parameters, and the like. For these purposes the graphics processor receives input from the user interface 38, such as patient name. The user interface is also coupled to the transmit controller 18 to control the generation of ultrasound signals from the transducer array 10' and hence the images produced by the transducer array and the ultrasound system. The transmit control function of the controller 18 is only one of the functions performed. The controller 18 also takes account of the mode of operation (given by the user) and the corresponding required transmitter configuration and band-pass configuration in the receiver analog to digital converter. The controller 18 can be a state machine with fixed states.

The user interface is also coupled to the multi-planar reformatter 44 for selection and control of the planes of multiple multi-planar reformatted (MPR) images which may be used to perform quantified measures in the image field of the MPR images.

The controller 18 may be further adapted to perform any part of the methods described below with reference to FIGS. 2 and 3. Alternatively, these methods may be performed by a separate controller, or a plurality of controllers. The user interface 38, or a separate user interface, may be adapted to receive a user input to alter the weightings used in the generation of the compound ultrasound images. The user interface may comprise a dial, slider or any other suitable means of adjusting a parameter. The user interface may be combined with the image display 40 by way of touch screen functionality. The system may further comprise storage means for storing predetermined weighting settings, which may be selected by the user by way of the user interface.

Figure 2:
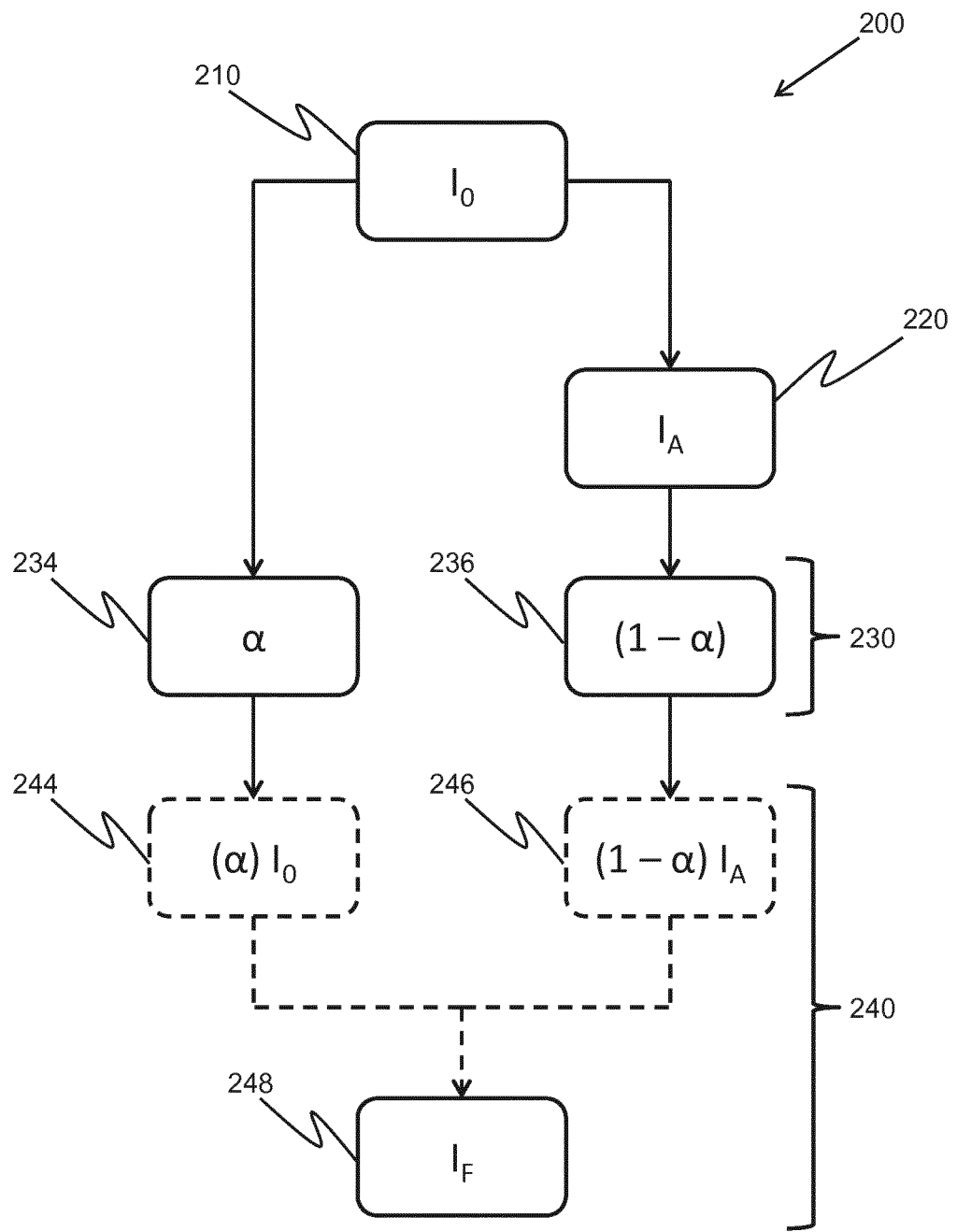
FIG. 2 shows a method of the invention.

FIG. 2 shows a method 200 for generating a compound ultrasound image.

In step 210, a first ultrasound image, $I_O$, is obtained, for example, by way of an ultrasonic probe 10.

In step 220, adaptive beamforming is applied to the first ultrasound image, thereby generating a second ultrasound image, $I_A$.

For example, minimum variance beamforming or coherence factor weighting may be applied to the first ultrasound image in order to generate the second ultrasound image.

In section 230, a weighting is determined based on the first and second ultrasound images, wherein the weighting comprises a weighting component. A first weighting component 234 may be determined for the first ultrasound image and a second weighting component 236 may be determined for the second ultrasound image. The first and second weighting components may depend on a single tuning parameter, $\alpha$.

For example, the first weighting component may be equal to a first tuning parameter, $\alpha$, wherein $0 \leq \alpha \leq 1$. In this case, the second weighting component may be equal to $(1-\alpha)$. In this way, the first and second weighting components may be controlled by a single parameter. This parameter may be controlled by a user of the ultrasound system of FIG. 1, for example, by way of the user interface 38. The user interface may comprise a dial adapted to alter the value of $\alpha$. By turning the dial in a first direction, the value of $\alpha$ may be increased, and by turning the dial in a second direction, opposite to the first, the value of $\alpha$ may be decreased. This enables the direct control of the weightings applied to the first and second ultrasound images. Alternatively, the user interface may comprise a slider or a digital interface to carry out this function.

In addition, the weights can be depth-dependent. For example, it may be possible to choose to use more of the original (first) ultrasound image at deep depths and more of the adaptively beamformed (second) ultrasound image at shallow depths. In this case, depth dependent user controls may be provided accordingly.

In section 240, the compound ultrasound image is generated based on the first and second ultrasound images and the weighting.

In step 244, the first weighting component, $\alpha$, is applied to the first ultrasound image, which has not undergone adaptive beamforming. In step 246, the second weighting component, $(1-\alpha)$, is applied to the second ultrasound image, which has undergone adaptive beamforming. Following these steps, in step 248, the weighted first and second ultrasound images are summed to form the compound ultrasound image, as shown in the following equation:

$$I_f = \alpha I_O + (1-\alpha) I_A,$$

where: $I_f$ is the compound ultrasound image; $\alpha$ is the first weighting component; $I_O$ is the first (original) ultrasound image; $(1-\alpha)$ is the second weighting component; and $I_A$ is the second (adaptively beamformed) ultrasound image.

Figure 3:
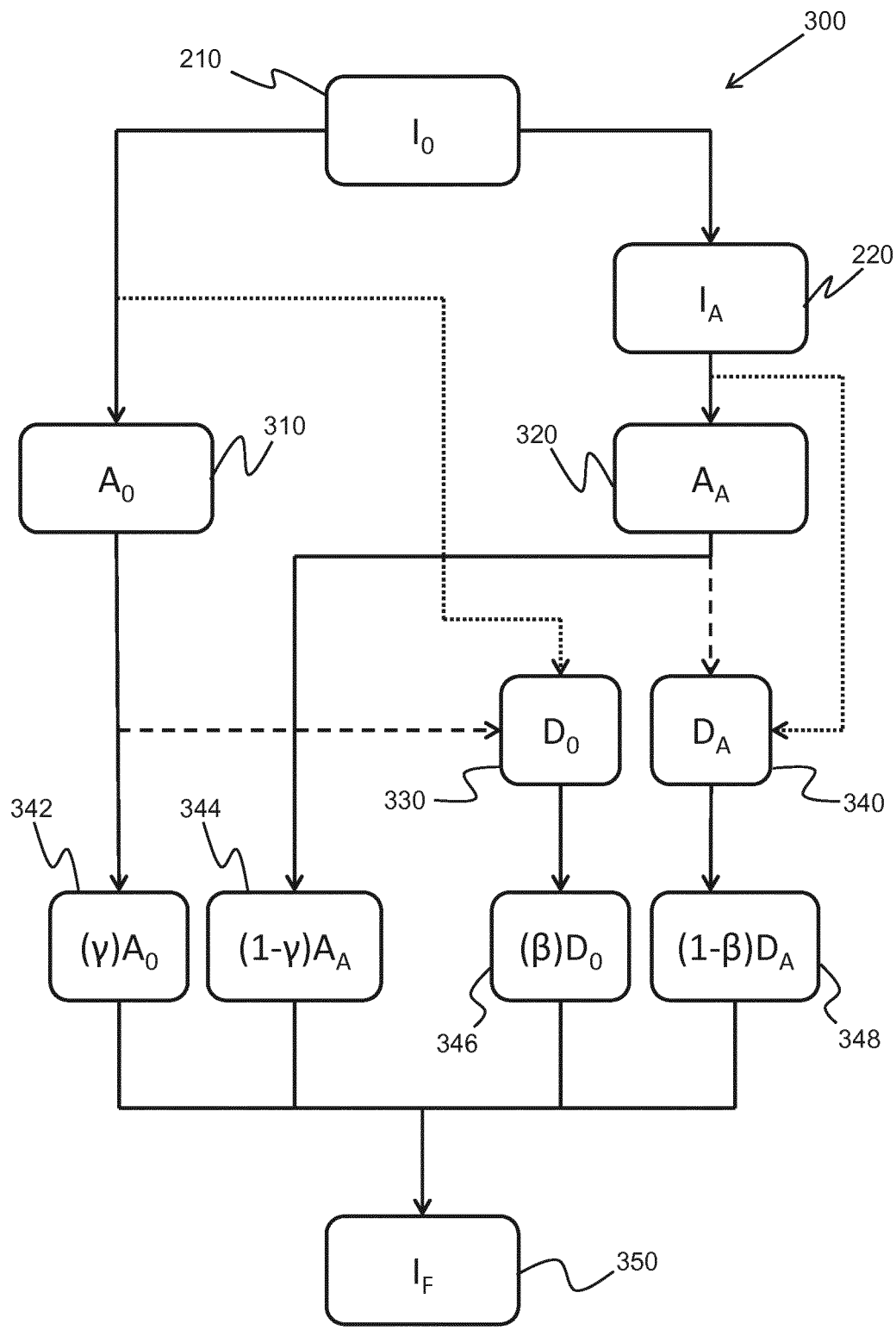
FIG. 3 shows an embodiment of the method shown in FIG. 2.

FIG. 3 shows an embodiment 300 of the method of FIG. 2.

This method enables the generation of the compound ultrasound image to be controlled separately at different spatial frequencies or differently for structures and speckle. Typically, the low spatial frequencies contain clutter, grating lobe, and noise artifacts in the hypoechoic areas of the images; and the high spatial frequencies contain the speckle noise and high-resolution objects. Separations between structures and speckle can alternatively be done with a resolution-preserving speckle smoothing filter such as a Lee filter.

The initial steps of obtaining a first ultrasound image 210 and generating a second ultrasound image 220 by way of adaptive beamforming are equivalent to the steps shown in FIG. 2.

In steps 310 and 320, a low pass filter or speckle smoothing filter is applied to the first and second ultrasound images, respectively. In this way, a first image approximation, $A_O$, and a second image approximation, $A_A$, which contain low spatial frequency or structural information are generated from the original and adaptively beamformed images.

In step 330, a first detail or speckle image, $D_O$, is generated based on the first image approximation and the first ultrasound image by subtracting the first image approximation from the first ultrasound image. In other words, the low spatial frequency information/the structures of the first image approximation are removed from the first ultrasound image, thereby resulting in an image containing only high spatial frequency information/only speckle.

In a similar manner, in step 340, a second detail image is generated based on the second image approximation and the second ultrasound image by subtracting the second image approximation from the second ultrasound image.

In steps 342 to 348, weighting components are applied to the first and second images approximations and the first and second detail images.

In steps 342 and 344, a third weighting component is applied to the first image approximation and a fourth weighting component is applied to the second image approximation. As described with reference to FIG. 2, these weighting components may be controlled by a single tuning parameter, $\gamma$.

In steps 346 and 348, a fifth weighting component is applied to the first detail image and a sixth weighting component is applied the second detail image. Once again, these weighting components may be controller by a single independent tuning parameter, $\beta$.

In other words, the low spatial frequency and high spatial frequency image contributions may be controlled independently from each other by way of the tuning parameters. This may provide a high level of control over the final image composition without requiring a large amount of complex input from the user.

In step 350, the weighted first and second detail images and first and second image approximations are summed, thereby generating the compound ultrasound image, as shown in the following equation:

$$I_f = \gamma A_O + (1-\gamma)A_A + \beta D_O + (1-\beta)D_A,$$

where: $\gamma$ is the third weighting component; $A_O$ is the first image approximation; $(1-\gamma)$ is the fourth weighting component; $A_A$ is the second image approximation; $\beta$ is the fifth weighting component; $D_O$ is the first detail image; $(1-\beta)$ is the sixth weighting component; and $D_A$ is the second detail image.

For example, when reduction is desired, a combined image that privileges the low spatial frequencies of the adaptively beamformed image, $A_A$, and the high spatial frequencies of the original image, $D_O$, may be preferred.

In addition, a speckle suppression control may be provided with another weighting component $\delta$:

$$I_f = \gamma A_O + (1-\gamma)A_A + \delta(\beta D_O + (1-\beta)D_A),$$

where $\delta < 1$ will contribute to speckle attenuation.

In practice, it is often desirable to privilege the low frequency features/structures of the high-contrast adaptively beamformed image, and the high frequency features of the original image so as to not enhance speckle noise. With that in mind, default weighting values may be set with $\gamma \approx 0$ and $\beta \approx 1$.

Alternatively, by default the high frequencies/speckle may be taken from the original image, and the user is given a choice to combine either the full original and adaptively beamformed images, or only the low spatial frequency/structure components of them. That is, a check box, or button, may be provided on the user interface 38 to enable a user to choose between, for example, the two operations shown below. In this case, the tuning parameter, $\alpha/\gamma$, may be controlled by a dial or slider on the user interface.

$$I_f = \alpha I_O + (1-\alpha)I_A \qquad \text{(full combination)}$$

$$I_f = \gamma A_O + (1-\gamma)A_A + D_O \text{(combination of the low frequency bands only)}$$

Upon initialization, the ultrasound system may access a database of predetermined weightings. The user may then select a predetermined weighting by way of the user interface. The database may be stored internally, such as in a memory, or externally, such as on a server accessible via the internet.

The predetermined weightings may comprise manually determined weightings from experienced users, which produce optimal image quality in a given imaging scenario. In addition, the ultrasound system may detect a current imaging scenario, based on the image content, and dynamically adapt the current weightings based on the optimized weightings used in a similar imaging scenario. This may be performed by determining a relationship between the input signals and the output weightings in the manually optimized cases and using this relationship to determine weightings for the current input signals. In other words, the ultrasound system may adapt the weightings based on the content of the image, thereby further increasing the ease of use of the system for an inexperienced user. This feature may be activated, or deactivated, by the user via the user interface, for example via a button or checkbox.

As discussed above, embodiments make use of a controller for performing the data processing steps.

The controller can be implemented in numerous ways, with software and/or hardware, to perform the various functions required. A processor is one example of a controller which employs one or more microprocessors that may be programmed using software (e.g., microcode) to perform the required functions. A controller may however be implemented with or without employing a processor, and also may be implemented as a combination of dedicated hardware to perform some functions and a processor (e.g., one or more programmed microprocessors and associated circuitry) to perform other functions.

Examples of controller components that may be employed in various embodiments of the present disclosure include, but are not limited to, conventional microprocessors, application specific integrated circuits (ASICs), and field-programmable gate arrays (FPGAs).

In various implementations, a processor or controller may be associated with one or more storage media such as volatile and non-volatile computer memory such as RAM, PROM, EPROM, and EEPROM. The storage media may be encoded with one or more programs that, when executed on one or more processors and/or controllers, perform at the required functions. Various storage media may be fixed within a processor or controller or may be transportable, such that the one or more programs stored thereon can be loaded into a processor or controller.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A method for controlling the generation of a compound ultrasonic image, the method comprising:
   obtaining a first ultrasound image;
   applying adaptive beamforming to the first ultrasound image, thereby generating a second ultrasound image;
   determining a weighting based on the first and second ultrasound images, wherein the weighting comprises at least one weighting component; and
   generating the compound ultrasound image based on the first and second ultrasound images and the at least one weighting component wherein the at least one weighting component and the generating of the compound ultrasound image are depth-dependent, wherein the method further comprises:
   applying a low pass or speckle smoothing filter to the first and second ultrasound images, thereby generating a first image approximation and a second image approximation;
   generating a first detail image, based on the first image approximation and the first ultrasound image; and
   generating a second detail image, based on the second image approximation and the second ultrasound image.

2. A method as claimed in claim 1, wherein the generating of the first and second detail images comprises:
   subtracting the first image approximation from the first ultrasound image, thereby generating the first detail image; and
   subtracting the second image approximation from the second ultrasound image, thereby generating the second detail image.

3. A method as claimed in claim 1, wherein the generating of the compound ultrasound image comprises:
   applying a third weighting component to the first image approximation;
   applying a fourth weighting component to the second image approximation;
   applying a fifth weighting component to the first detail image;
   applying a sixth weighting component to the second detail image; and
   summing the weighted first and second detail images and first and second image approximations, thereby generating the compound ultrasound image.

4. A method as claimed in claim 3, wherein the third and fourth weighting component depend on a second tuning parameter, and,
   wherein the fifth and sixth weighting component depend on a third tuning parameter.

* * * * *